US008712069B1

(12) United States Patent
Murgia et al.

(10) Patent No.: US 8,712,069 B1
(45) Date of Patent: *Apr. 29, 2014

(54) SELECTION OF SYSTEM PARAMETERS BASED ON NON-ACOUSTIC SENSOR INFORMATION

(75) Inventors: Carlo Murgia, Sunnyvale, CA (US); Michael M. Goodwin, Scotts Valley, CA (US); Peter Santos, Los Altos, CA (US); Dana Massie, Santa Cruz, CA (US)

(73) Assignee: Audience, Inc., Mountain View, CA (US)

( * ) Notice: Subject to any disclaimer, the term of this patent is extended or adjusted under 35 U.S.C. 154(b) by 695 days.

This patent is subject to a terminal disclaimer.

(21) Appl. No.: 12/843,819

(22) Filed: Jul. 26, 2010

Related U.S. Application Data

(60) Provisional application No. 61/325,742, filed on Apr. 19, 2010.

(51) Int. Cl.
*A61F 11/06* (2006.01)

(52) U.S. Cl.
USPC ............. 381/71.1; 381/71.9; 702/92; 702/93; 702/94

(58) Field of Classification Search
USPC ................. 381/26, 91–92, 95, 17, 71.1, 71.9, 381/71.11, 71.12, 71.14, 103; 700/94; 704/226, 205; 702/92–99, 135, 702/141–143, 149–159, 189–199
See application file for complete search history.

(56) References Cited

U.S. PATENT DOCUMENTS

| | | | | |
|---|---|---|---|---|
| 7,246,058 | B2 * | 7/2007 | Burnett | 704/226 |
| 8,577,677 | B2 * | 11/2013 | Kim et al. | 704/228 |
| 2003/0169891 | A1 * | 9/2003 | Ryan et al. | 381/92 |
| 2004/0052391 | A1 * | 3/2004 | Bren et al. | 381/331 |
| 2006/0217977 | A1 * | 9/2006 | Gaeta et al. | 704/233 |
| 2008/0173717 | A1 * | 7/2008 | Antebi et al. | 235/439 |
| 2009/0055170 | A1 * | 2/2009 | Nagahama | 704/226 |
| 2010/0128881 | A1 * | 5/2010 | Petit et al. | 381/56 |
| 2010/0128894 | A1 * | 5/2010 | Petit et al. | 381/92 |
| 2010/0315905 | A1 * | 12/2010 | Lee et al. | 367/127 |

* cited by examiner

*Primary Examiner* — Vivian Chin
*Assistant Examiner* — Friedrich W Fahnert
(74) *Attorney, Agent, or Firm* — Carr & Ferrell LLP

(57) ABSTRACT

An audio processing system processes an audio signal that may come from one or more microphones. The audio processing system may use information from one or more non-acoustic sensors to improve a variety of system characteristics, including responsiveness and quality. Especially those audio processing systems that use spatial information, for example to separate multiple audio sources, are undesirably susceptible to changes in the relative position of any audio sources, the audio processing system itself, or any combination thereof. Using the non-acoustic sensor information may decrease this susceptibility advantageously in an audio processing system.

18 Claims, 6 Drawing Sheets

400

SELECTION OF SYSTEM PARAMETERS BASED ON NON-ACOUSTIC SENSOR INFORMATION

CROSS REFERENCE TO RELATED APPLICATION

This application claims the benefit of U.S. Provisional Application No. 61/325,742, filed on Apr. 19, 2010, entitled "Selection of System Parameters According to Non-Microphone Sensor Information," having inventors Carlo Murgia, Michael M. Goodwin, Peter Santos, and Dana Massie, which is hereby incorporated herein by reference in its entirety.

BACKGROUND

Communication devices that capture and transmit and/or store acoustic signals often use noise reduction techniques to provide a higher quality (i.e., less noisy) signal. Noise reduction may improve the audio quality in communication devices such as mobile telephones which convert analog audio to digital audio data streams for transmission over mobile telephone networks.

A device that receives an acoustic signal through a microphone can process the acoustic signal to distinguish between a desired and an undesired component. A noise reduction system based on acoustic information alone can be misguided or slow to respond to certain changes in environmental conditions.

There is a need to increase the quality and responsiveness of noise reduction systems to changes in environmental conditions.

SUMMARY OF THE INVENTION

The systems and methods of the present technology provide audio processing of an acoustic signal by non-acoustic sensor information. A system may receive and analyze an acoustic signal and information from a non-acoustic sensor, and process the acoustic signal based on the sensor information.

In some embodiments, the present technology provides methods for audio processing that may include receiving a first acoustic signal from a microphone. Information from a non-acoustic sensor may be received. The acoustic signal may be modified based on an analysis of the acoustic signal and the sensor information.

In some embodiments, the present technology provides systems for audio processing of an acoustic signal that may include a first microphone, a first sensor, and one or more executable modules that process the acoustic signal. The first microphone transduces an acoustic signal, wherein the acoustic signal includes a desired component and an undesired component. The first sensor provides non-acoustic sensor information. The one or more executable modules process the acoustic signal based on the non-acoustic sensor information.

DESCRIPTION OF EXEMPLARY EMBODIMENTS

Figure 1:
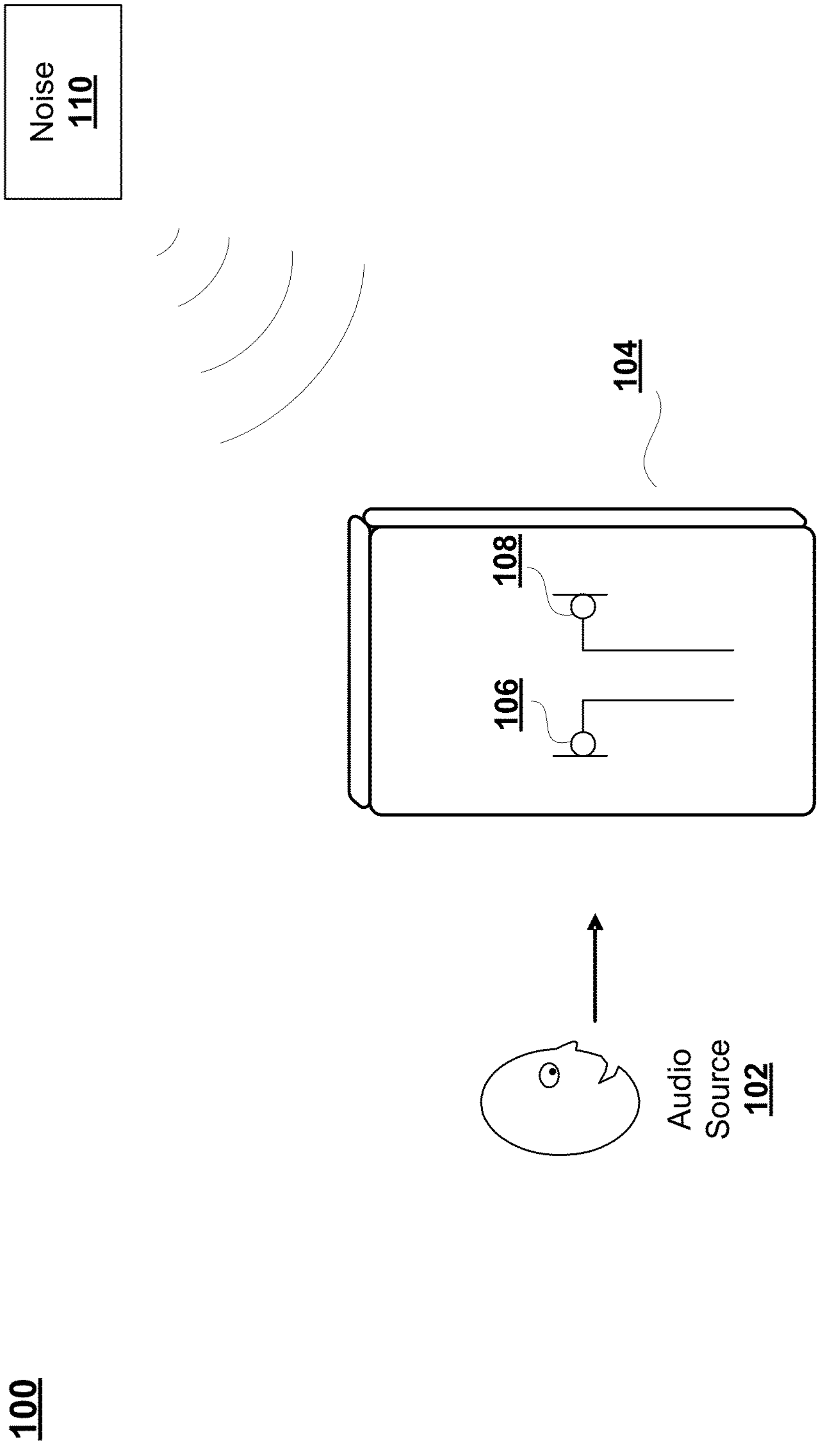
FIG. 1 illustrates an environment in which embodiments of the present technology may be practiced.

The present technology provides audio processing of an acoustic signal based at least in part on non-acoustic sensor information. By analyzing not only an acoustic signal but also information from a non-acoustic sensor, processing of the audio signal may be improved. The present technology can be applied in single-microphone systems and multi-microphone systems that transform acoustic signals to the frequency domain, to the cochlear domain, or any other domain. The processing based on non-acoustic sensor information allows the present technology to be more robust and provide a higher quality audio signal in environments where the system or any acoustic sources are subject to motion during use.

Audio processing as performed in the context of the present technology may be used in noise reduction systems, including noise cancellation and noise suppression. A brief description of both noise cancellation systems and noise suppression systems is provided below. Note that the audio processing system discussed herein may use both.

Noise reduction may be implemented by subtractive noise cancellation or multiplicative noise suppression. Noise cancellation may be based on null processing, which involves cancelling an undesired component in an acoustic signal by attenuating audio from a specific direction, while simultaneously preserving a desired component in an acoustic signal, e.g. from a target location such as a main speaker. Noise suppression may use gain masks multiplied against a sub-band acoustic signal to suppress the energy levels of noise (i.e. undesired) components in the sub-band signals. Both types of noise reduction systems may benefit from implementing the present technology.

Information from the non-acoustic sensor may be used to determine one or more audio processing system parameters. Examples of system parameters that may be modified based on non-acoustic sensor data are gain (PreGain Amplifier or PGA control parameters and/or Digital Gain control of primary and secondary microphones), inter-level difference (ILD) equalization, directionality coefficients (for null processing), and thresholds or other factors that control the classification of echo vs. noise and noise vs. speech.

An audio processing system using spatial information, for example to separate multiple audio sources, may be susceptible to a change in the relative position of the communication device that includes the audio processing system. Decreasing this susceptibility is referred to as increasing the positional robustness. The operating assumptions and parameters of the underlying algorithm that are implemented by an audio processing system need to be changed according to the new relative position of the communication device that incorporates the audio processing system. Analyzing only acoustic signals may lead to ambiguity about the current operating conditions or a slow response to a change in the current operating conditions of an audio processing system. Incorporating information from one or more non-acoustic sensors may remove some or all of the ambiguity and/or improve response time and therefore improve the effectiveness and/or quality of the system.

FIG. 1 illustrates an environment 100 in which embodiments of the present technology may be practiced. FIG. 1 includes audio source 102, exemplary communication device 104, and noise source 110. The audio source 102 may be a user speaking in the vicinity of a communication device 104. Audio from the user or main talker may be called main speech. The exemplary communication device 104 as illustrated includes two microphones: a primary microphone 106 and a secondary microphone 108 located a distance away from the primary microphone 106. In other embodiments, the communication device 104 may include one or more than two microphones, such as for example three, four, five, six, seven, eight, nine, ten or even more microphones.

The primary microphone 106 and secondary microphone 108 may be omni-directional microphones. Alternatively, embodiments may utilize other forms of microphones or acoustic sensors/transducers. While the microphones 106 and 108 receive and transduce sound (i.e. an acoustic signal) from audio source 102, microphones 106 and 108 also pick up noise 110. Although noise 110 is shown coming from a single location in FIG. 1, it may comprise any undesired sounds from one or more locations different from audio source 102, and may include sounds produced by a loudspeaker associated with device 104, and may also include reverberations and echoes. Noise 110 may be stationary, non-stationary, and/or a combination of both stationary and non-stationary. Echo resulting from a far-end talker is typically non-stationary.

Some embodiments may utilize level differences (e.g. energy differences) between the acoustic signals received by microphones 106 and 108. Because primary microphone 106 may be closer to audio source 102 than secondary microphone 108, the intensity level is higher for primary microphone 106, resulting in a larger energy level received by primary microphone 106 when the main speech is active, for example. The inter-level difference (ILD) may be used to discriminate speech and noise. An audio processing system may use a combination of energy level differences and time delays to identify speech components. An audio processing system may additionally use phase differences between the signals coming from different microphones to distinguish noise from speech, or distinguish one noise source from another noise source. Based on analysis of such inter-microphone differences, which can be referred to as binaural cues, speech signal extraction or speech enhancement may be performed.

Figure 2:
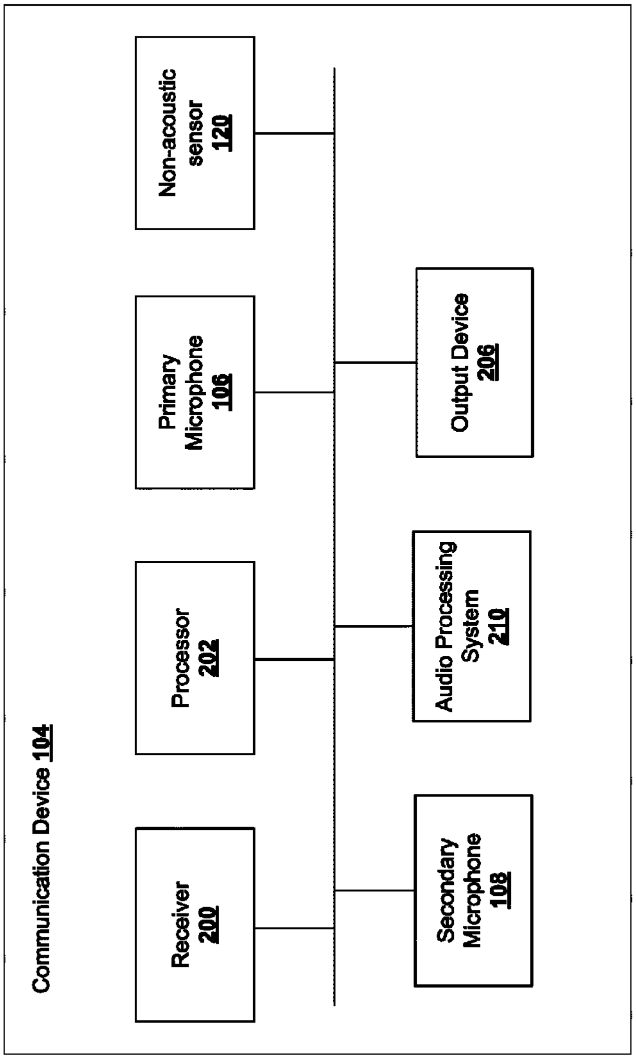
FIG. 2 is a block diagram of an exemplary communication device.

FIG. 2 is a block diagram of an exemplary communication device 104. In exemplary embodiments, communication device 104 (also shown in FIG. 1) is an audio receiving device that includes a receiver 200, a processor 202, a primary microphone 106, a secondary microphone 108, an audio processing system 210, a non-acoustic sensor 120, and an output device 206. Communication device 104 may comprise more or other components necessary for its operations. Similarly, communication device 104 may comprise fewer components that perform similar or equivalent functions to those depicted in FIG. 2. Additional details regarding each of the elements in FIG. 2 is provided below.

Processor 202 in FIG. 2 may include hardware and/or software which implements the processing function, and may execute a program stored in memory (not pictured in FIG. 2). Processor 202 may use floating point operations, complex operations, and other operations. The exemplary receiver 200 may be configured to receive a signal from a communication network. In some embodiments, the receiver 200 may include an antenna device (not shown) for communicating with a wireless communication network, such as for example a cellular communication network. The signals received by receiver 200 and microphones 106 and 108 may be processed by audio processing system 210 and provided as output by output device 206. For example, audio processing system 210 may implement noise reduction techniques on the received signals. The present technology may be used in both the transmit path and receive path of a communication device.

Non-acoustic sensor 120 may measure a spatial position or change in position of a microphone relative to the spatial position of an audio source, such as the mouth of a main speaker (a.k.a the "Mouth Reference Point" or MRP). The information measured by non-acoustic sensor 120 may be provided to processor 202 or stored in memory. As the microphone moves relative to the MRP, processing of the audio signal may be adapted accordingly. Generally, a non-acoustic sensor 120 may be implemented as a motion sensor, a (visible or infra-red) light sensor, a proximity sensor, a gyroscope, a level sensor, a compass, a Global Positioning System (GPS) unit, or an accelerometer. Alternatively, an embodiment of the present technology may combine sensor information of multiple non-acoustic sensors to determine when and how to modify the acoustic signal, or modify and/or select any system parameter of the audio processing system.

Audio processing engine 210 in FIG. 2 may furthermore be configured to receive acoustic signals from an acoustic source via the primary and secondary microphones 106 and 108 (e.g., primary and secondary acoustic sensors) and process the acoustic signals. Primary and secondary microphones 106 and 108 may be spaced a distance apart such that acoustic waves impinging on the device from certain directions have different energy levels at the two microphones. After reception by microphones 106 and 108, the acoustic signals may be converted into electric signals (i.e., a primary electric signal and a secondary electric signal). These electric signals may themselves be converted by an analog-to-digital converter (not shown) into digital signals for processing in accordance with some embodiments. In order to differentiate the acoustic signals, the acoustic signal received by primary microphone 106 is herein referred to as the primary acoustic signal, while the acoustic signal received by secondary microphone 108 is herein referred to as the secondary acoustic signal. Embodiments of the present invention may be practiced with any number of microphones/audio sources.

In various embodiments, where the primary and secondary microphones are omni-directional microphones that are closely spaced (e.g., 1-2 cm apart), a beamforming technique may be used to simulate a forward-facing and a backward-facing directional microphone response. A level difference may be obtained using the simulated forward-facing and the backward-facing directional microphone. The level difference may be used to discriminate speech and noise in e.g. the time-frequency domain, which can be used in noise and/or echo reduction.

Output device 206 in FIG. 2 is any device that provides an audio output to a listener. For example, the output device 206 may comprise a speaker, an earpiece of a headset, or handset on communication device 104. In some embodiments, the acoustic signals from output device 206 may be included as part of the (primary or secondary) acoustic signal recorded by microphones 106 and 108. This may cause echoes, which are generally undesirable. The primary acoustic signal and the secondary acoustic signal may be processed by audio processing system 210 to produce a signal with an improved audio quality for transmission across a communications network and/or routing to output device 206. The present technology may be used, e.g. in audio processing system 210, to improve the audio quality of the primary and secondary acoustic signal.

Embodiments of the present invention may be practiced on any device configured to receive and/or provide audio such as, but not limited to, cellular phones, phone handsets, headsets, and systems for teleconferencing applications. While some embodiments of the present technology are described in reference to operation on a cellular phone, the present technology may be practiced on any communication device.

Some or all of the above-described modules in FIG. 2 may be comprised of instructions that are stored on storage media. The instructions can be retrieved and executed by the processor 202. Some examples of instructions include software, program code, and firmware. Some examples of storage media comprise memory devices and integrated circuits. The instructions are operational when executed by processor 202 to direct processor 202 to operate in accordance with embodiments of the present invention. Those skilled in the art are familiar with instructions, processor(s), and (computer readable) storage media.

Figure 3:
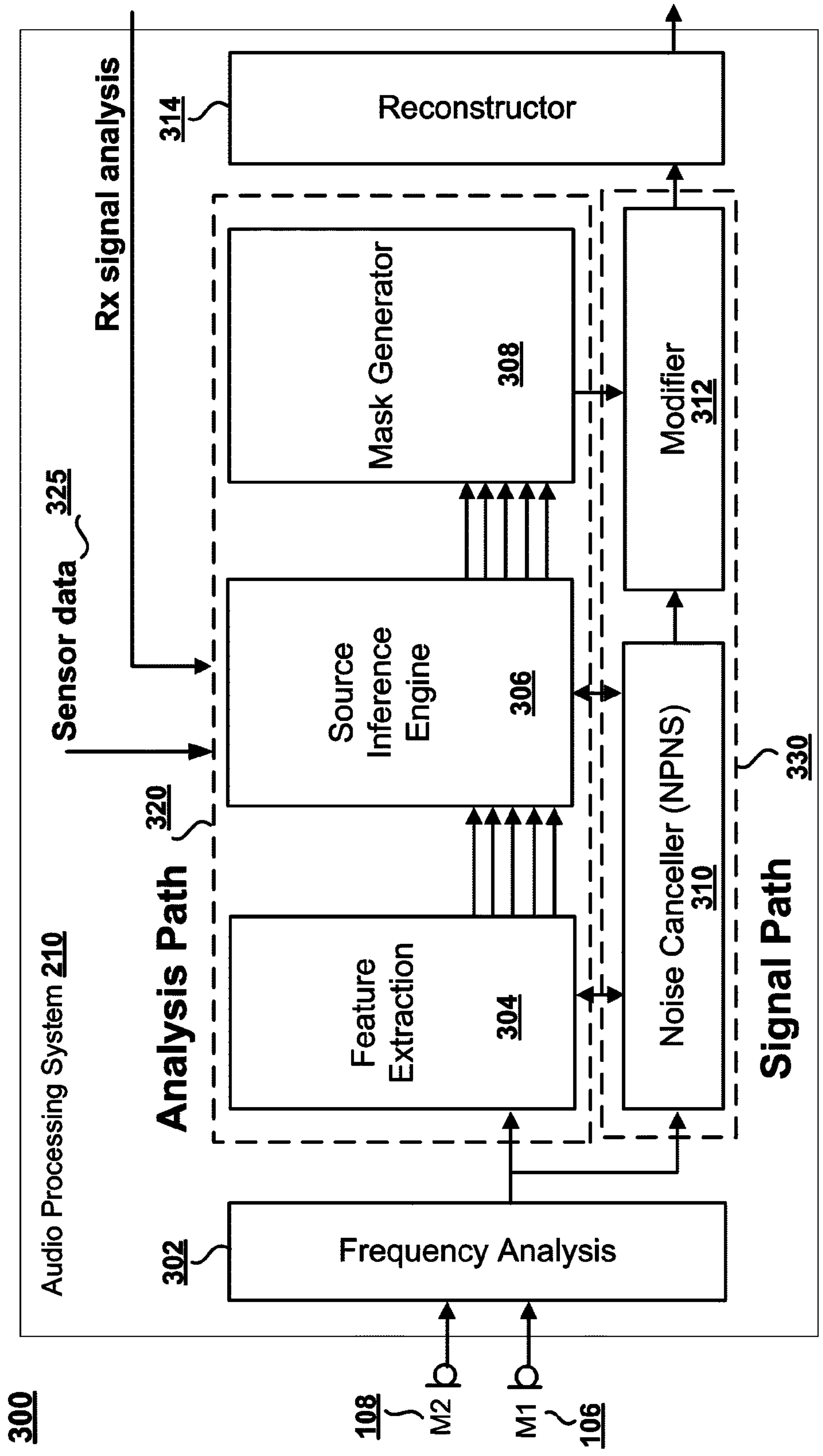
FIG. 3 is a block diagram of an exemplary audio processing system.

FIG. 3 is a block diagram of an exemplary audio processing system 210. In exemplary embodiments, the audio processing system 210 (also shown in FIG. 2) may be embodied within a memory device inside communication device 104. Audio processing system 210 may include a frequency analysis module 302, a feature extraction module 304, a source inference engine module 306, a mask generator module 308, noise canceller (Null Processing Noise Subtraction or NPNS) module 310, modifier module 312, and reconstructor module 314. Descriptions for these modules are provided below.

Audio processing system 210 may include more or fewer components than illustrated in FIG. 3, and the functionality of modules may be combined or expanded into fewer or additional modules. Exemplary lines of communication are illustrated between various modules of FIG. 3, and in other figures herein. The lines of communication are not intended to limit which modules are communicatively coupled with others, nor are they intended to limit the number of and type of signals communicated between modules.

Data provided by non-acoustic sensor 120 (FIG. 2) may be used in audio processing system 210, for example by analysis path sub-system 320. This is illustrated in FIG. 3 by sensor data 325, which may be provided by non-acoustic sensor 120, leading into analysis path sub-system 320. Utilization of non-acoustic sensor information is discussed in more detail below, for example with respect to Noise Canceller 310 and the equalization charts of FIG. 4.

In the audio processing system of FIG. 3, acoustic signals received from primary microphone 106 and secondary microphone 108 are converted to electrical signals, and the electrical signals are processed by frequency analysis module 302. In one embodiment, frequency analysis module 302 takes the acoustic signals and mimics the frequency analysis of the cochlea (e.g., cochlear domain), simulated by a filter bank. Frequency analysis module 302 separates each of the primary and secondary acoustic signals into two or more frequency sub-band signals. A sub-band signal is the result of a filtering operation on an input signal, where the bandwidth of the filter is narrower than the bandwidth of the signal received by the frequency analysis module 302. Alternatively, other filters such as a short-time Fourier transform (STFT), sub-band filter banks, modulated complex lapped transforms, cochlear models, wavelets, etc., can be used for the frequency analysis and synthesis.

Because most sounds (e.g. acoustic signals) are complex and include more than one frequency, a sub-band analysis of the acoustic signal determines what individual frequencies are present in each sub-band of the complex acoustic signal during a frame (e.g. a predetermined period of time). For example, the duration of a frame may be 4 ms, 8 ms, or some other length of time. Some embodiments may not use a frame at all. Frequency analysis module 302 may provide sub-band signals in a fast cochlea transform (FCT) domain as an output.

Frames of sub-band signals are provided by frequency analysis module 302 to an analysis path sub-system 320 and to a signal path sub-system 330. Analysis path sub-system 320 may process a signal to identify signal features, distinguish between speech components and noise components of the sub-band signals, and generate a signal modifier. Signal path sub-system 330 modifies sub-band signals of the primary acoustic signal, e.g. by applying a modifier such as a multiplicative gain mask or a filter, or by using subtractive signal components as may be generated in analysis path sub-system 320. The modification may reduce undesired components (i.e. noise) and preserve desired speech components (i.e. main speech) in the sub-band signals.

Noise suppression can use gain masks multiplied against a sub-band acoustic signal to suppress the energy levels of noise (i.e. undesired) components in the subband signals. This process is also referred to as multiplicative noise suppression. In some embodiments, acoustic signals can be modified by other techniques, such as a filter. The energy level of a noise component may be reduced to less than a residual noise target level, which may be fixed or slowly time-varying. A residual noise target level may for example be defined as a level at which the noise component ceases to be audible or perceptible, below a self-noise level of a microphone used to capture the acoustic signal, or below a noise gate of a component such as an internal Automatic Gain Control (AGC) noise gate or baseband noise gate within a system used to perform the noise cancellation techniques described herein.

Signal path sub-system 330 within audio processing system 210 of FIG. 3 includes NPNS module 310 and modifier module 312. NPNS module 310 receives sub-band frame signals from frequency analysis module 302. NPNS module 310 may subtract (e.g., cancel) an undesired component (i.e. noise) from one or more sub-band signals of the primary acoustic signal. As such, NPNS module 310 may output sub-band estimates of noise components in the primary signal and sub-band estimates of speech components in the form of noise-subtracted sub-band signals.

NPNS module 310 within signal path sub-system 330 may be implemented in a variety of ways. In some embodiments, NPNS module 310 may be implemented with a single NPNS module. Alternatively, NPNS module 310 may include two or more NPNS modules, which may be arranged for example in a cascaded fashion. NPNS module 310 can provide noise cancellation for two-microphone configurations, for example based on source location, by utilizing a subtractive algorithm. It can also provide echo cancellation. Since noise and echo cancellation can usually be achieved with little or no voice quality degradation, processing performed by NPNS module 310 may result in an increased signal-to-noise-ratio (SNR) in the primary acoustic signal received by subsequent post-filtering and multiplicative stages, some of which are shown elsewhere in FIG. 3. The amount of noise cancellation performed may depend on the diffuseness of the noise source and the distance between microphones. These both contribute towards the coherence of the noise between the microphones, with greater coherence resulting in better cancellation by the NPNS module.

An example of null processing noise subtraction performed in some embodiments by the NPNS module 310 is disclosed in U.S. application Ser. No. 12/422,917, entitled "Adaptive Noise Cancellation," filed Apr. 13, 2009, which is incorporated herein by reference.

Noise cancellation may be based on null processing, which involves cancelling an undesired component in an acoustic signal by attenuating audio from a specific direction, while simultaneously preserving a desired component in an acoustic signal, e.g. from a target location such as a main speaker. The desired audio signal may be a speech signal. Null processing noise cancellation systems can determine a vector that indicates the direction of the source of an undesired component in an acoustic signal. This vector is referred to as a spatial "null" or "null vector." Audio from the direction of the spatial null is subsequently reduced. As the source of an undesired component in an acoustic signal moves relative to the position of the microphone(s), a noise reduction system can track the movement, and adapt and/or update the corresponding spatial null accordingly.

An example of a multi-microphone noise cancellation system which performs null processing noise subtraction (NPNS) is described in U.S. patent application Ser. No. 12/215,980, entitled "System and Method for Providing Noise Suppression Utilizing Null Processing Noise Subtraction," filed Jun. 30, 2008, which is incorporated by reference herein. Noise subtraction systems can operate effectively in dynamic conditions and/or environments by continually interpreting the conditions and/or environment and adapting accordingly.

Information from non-acoustic sensor 120 may be used to control the direction of a spatial null in a noise canceller 310. In particular, the non-acoustic sensor information may be used to direct a null in an NPNS module or a synthetic cardioid system based on positional information provided by sensor 120. An example of a synthetic cardioid system is described in U.S. patent application Ser. No. 11/699,732, entitled "System and Method for Utilizing Omni-Directional Microphones for Speech Enhancement," filed Jan. 29, 2007, which is incorporated by reference herein.

In a two-microphone directional system, coefficients σ and α may have complex values. The coefficients may represent the transfer functions from a primary microphone signal (P) to a secondary (S) microphone signal in a two-microphone representation. However, the coefficients may also be used in an N microphone system. The goal of the σ coefficient(s) is to cancel the speech signal component captured by the primary microphone from the secondary microphone signal. The cancellation can be represented as S-σP. The output of this subtraction is then an estimate of the noise in the acoustic environment. The α coefficient is used to cancel the noise from the primary microphone signal using this noise estimate. The ideal σ and α coefficients can be derived using adaptation rules, wherein adaptation may be necessary to point the σ null in the direction of the speech source and the α null in the direction of the noise.

In adverse SNR conditions, it becomes difficult to keep the system working optimally, i.e. optimally cancelling the noise and preserving the speech. In general, since speech cancellation is the most undesirable behavior, the system is tuned in order to minimize speech loss. Even with conservative tuning, however, noise leakage can occur.

As an alternative, a spatial map of the σ (and potentially α) coefficients can be created in the form of a table, comprising one set of coefficients per valid position. Each combination of coefficients may represent a position of the microphone(s) of the communication device relative to the MRP and/or a noise source. From the full set entailing all valid positions, an optimal set of values can be created, for example using the LBG algorithm. The size of the table may vary depending on the computation and memory resources available in the system. For example, the table could contain u and a coefficients describing all possible positions of the phone around the head. The table could then be indexed using three-dimensional and proximity sensor data.

Analysis path sub-system 320 in FIG. 3 includes feature extraction module 304, source interference engine module 306, and mask generator module 308. Feature extraction module 304 receives the sub-band frame signals derived from the primary and secondary acoustic signals provided by frequency analysis module 302 and receives the output of NPNS module 310. The feature extraction module 304 may compute frame energy estimations of the sub-band signals, an inter-microphone level difference (ILD) between the primary acoustic signal and the secondary acoustic signal, and self-noise estimates for the primary and second microphones. Feature extraction module 304 may also compute other monaural or binaural features for processing by other modules, such as pitch estimates and cross-correlations between microphone signals. Feature extraction module 304 may both provide inputs to and process outputs from NPNS module 310, as indicated by a double-headed arrow in FIG. 3.

Feature extraction module 304 may compute energy levels for the sub-band signals of the primary and secondary acoustic signal and an inter-microphone level difference (ILD) from the energy levels. The ILD may be determined by feature extraction module 304. Determining energy level estimates and inter-microphone level differences is discussed in more detail in U.S. patent application Ser. No. 11/343,524, entitled "System and Method for Utilizing Inter-Microphone Level Differences for Speech Enhancement", which is incorporated by reference herein.

Non-acoustic sensor information may be used to configure a gain of a microphone signal as processed, for example by feature extraction module 304. Specifically, in multi-microphone systems that use ILD as a source discrimination cue, the level of the main speech decreases as the distance from the primary microphone to the MRP increases. If the distance from all microphones to the MRP increases, the ILD of the main speech decreases, resulting in less discrimination between the main speech and the noise sources. Such corruption of the ILD cue typically leads to undesirable speech loss. Increasing the gain of the primary microphone modifies the ILD in favor of the primary microphone. This results in less noise suppression, but improves positional robustness.

Another part of analysis path sub-system 320 is source inference engine module 306, which may process frame energy estimations to compute noise estimates, and which may derive models of the noise and speech in the sub-band signals. The frame energy estimate processed in module 306 may include the energy estimates of the output of the frequency analysis 302 and of the noise canceller 310. Source inference engine module 306 adaptively estimates attributes of the acoustic sources. The energy estimates may be used in conjunction with the speech models, noise models, and other attributes estimated in module 306 to generate a multiplicative mask in mask generator module 308.

Source inference engine module 306 in FIG. 3 may receive the ILD from feature extraction module 304 and track the ILD-probability distributions or "clusters" of audio source 102, noise 110 and optionally echo. When ignoring echo, without any loss of generality, when the source and noise ILD-probability distributions are non-overlapping, it is possible to specify a classification boundary or dominance threshold between the two distributions. The classification boundary or dominance threshold is used to classify an audio signal as speech if the ILD is sufficiently positive or as noise if the ILD is sufficiently negative. The classification may be determined per sub-band and time frame and used to form a dominance mask as part of a cluster tracking process.

The classification may additionally be based on features extracted from one or more non-acoustic sensors, and as a result, the audio processing system may exhibit improved positional robustness. Source interference engine module 306 performs an analysis of sensor data 325, depending on which system parameters are intended to be modified based on the non-acoustic sensor data.

Source interference engine module 306 may provide the generated classification to NPNS module 310, and may utilize the classification to estimate noise in NPNS output signals. A current noise estimate along with locations in the energy spectrum where the noise may be located are provided for processing a noise signal within audio processing system 210. Tracking clusters is described in U.S. patent application Ser. No. 12/004,897, entitled "System and method for Adaptive Classification of Audio Sources," filed on Dec. 21, 2007, the disclosure of which is incorporated herein by reference.

Source inference engine module 306 may generate an ILD noise estimator and a stationary noise estimate. In one embodiment, the noise estimates are combined with a max( ) operation, so that the noise suppression performance resulting from the combined noise estimate is at least that of the individual noise estimates. The ILD noise estimate is derived from the dominance mask and the output of NPNS module 310.

For a given normalized ILD, sub-band, and non-acoustical sensor information, a corresponding equalization function may be applied to the normalized ILD signal to correct distortion. The equalization function may be applied to the normalized ILD signal by either the source inference engine 306 or mask generator 308. Using non-acoustical sensor information to apply an equalization function is discussed in more detail with respect to FIG. 4.

Mask generator module 308 of analysis path sub-system 320 may receive models of the sub-band speech components and/or noise components as estimated by source inference engine module 306. Noise estimates of the noise spectrum for each sub-band signal may be subtracted out of the energy estimate of the primary spectrum to infer a speech spectrum. Mask generator module 308 may determine a gain mask for the sub-band signals of the primary acoustic signal and provide the gain mask to modifier module 312. Modifier module 312 multiplies the gain masks and the noise-subtracted sub-band signals of the primary acoustic signal output by the NPNS module 310, as indicated by the arrow from NPNS module 310 to modifier module 312. Applying the mask reduces the energy levels of noise components in the sub-band signals of the primary acoustic signal and thus accomplishes noise reduction.

Values of the gain mask output from mask generator module 308 may be time-dependent and sub-band-signal-dependent, and may optimize noise reduction on a per sub-band basis. Noise reduction may be subject to the constraint that the speech loss distortion complies with a tolerable threshold limit. The threshold limit may be based on many factors. Noise reduction may be less than substantial when certain conditions, such as unacceptably high speech loss distortion, do not allow for more noise reduction. In various embodiments, the energy level of the noise component in the sub-band signal may be reduced to less than a residual noise target level. In some embodiments, the residual noise target level is the same for each sub-band signal.

Reconstructor module 314 converts the masked frequency sub-band signals from the cochlea domain back into the time domain. The conversion may include applying gains and phase shifts to the masked frequency sub-band signals adding the resulting signals. Once conversion to the time domain is completed, the synthesized acoustic signal may be provided to the user via output device 206 and/or provided to a codec for encoding.

In some embodiments, additional post-processing of the synthesized time domain acoustic signal may be performed. For example, comfort noise generated by a comfort noise generator may be added to the synthesized acoustic signal prior to providing the signal to the user. Comfort noise may be a uniform constant noise that is not usually discernable to a listener (e.g., pink noise). This comfort noise may be added to the synthesized acoustic signal to enforce a threshold of audibility and to mask low-level non-stationary output noise components. In some embodiments, the comfort noise level may be chosen to be just above a threshold of audibility and/or may be settable by a user.

The audio processing system of FIG. 3 may process several types of signals in a communication device. The system may process signals, such as a digital Rx signal, received through an antenna or other connection. The system may also process sensor data from one or more non-acoustic sensors, such as a motion sensor, a light sensor, a proximity sensor, a gyroscope, a level sensor, a compass, a GPS unit, or an accelerometer. A non-acoustic sensor 120 is shown as part of communication device 104 in FIG. 2. By including non-acoustic sensor data 325 (FIG. 3) as input to analysis path sub-system 320, any of the modules contained therein may benefit and improve its efficiency and/or the quality of its outputs. Several examples of (audio processing) system parameter selection and/or modification in response to non-acoustic sensor information are presented below.

In some embodiments, noise may be reduced in acoustic signals received by audio processing system 210 by a system that adapts over time. Audio processing system 210 may perform noise suppression and noise cancellation using initial values of parameters, which may be adapted over time based on information received from non-acoustic sensor 120, processing of the acoustic signal, and a combination of sensor 120 information and acoustic signal processing.

Figure 4:
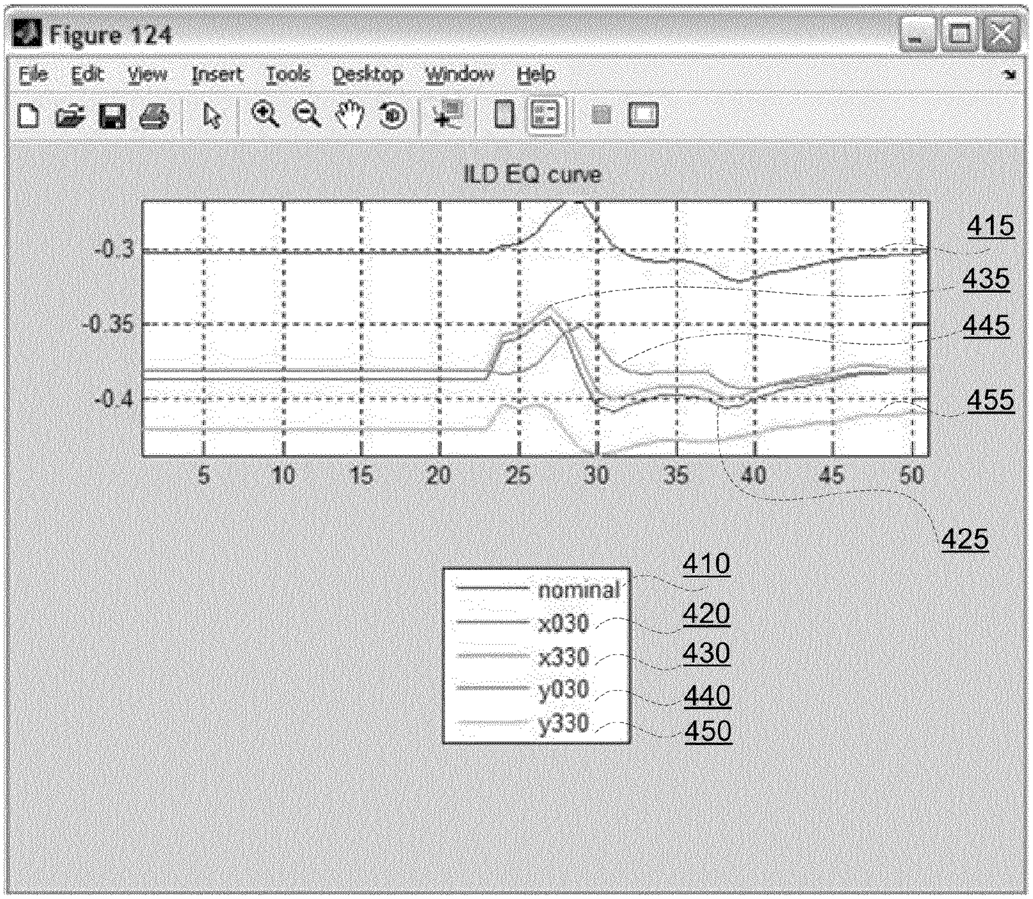
FIG. 4 is a chart illustrating equalization curves for signal modification.

Non-acoustic sensor 120 may provide information to control application of an equalization function to ILD sub-band signals. FIG. 4 is a chart 400 illustrating equalization curves for signal modification. When a system uses ILD information per sub-band to distinguish between desired and undesired components in an acoustic signal, ILD equalization per sub-band may be used to correct ILD distortion introduced by the acoustic characteristics of the head of the user providing the (desired) main speech. After equalization, the ILD for the main speech is ideally a known positive value. Regularized equalization improves the quality of the classification of main speech and undesired components in an acoustic signal.

The curves illustrated in FIG. 4 may be associated with different detected positions, each curve representing a different equalization to apply to a normalized ILD. The usual position of a communication device and its microphones relative to the mouth of the user (or "Mouth Reference Point" or MRP) is called the nominal position (which could for example be defined by the axis going from the "Ear Reference Point" or ERP to the MRP). Two common ways to change the nominal position are rotating the communication device around the user's ear (i.e. around the ear point), along the vertical plane next to the user's head, and, secondly, tilting the microphone(s) of the communication device away from the user's mouth by pivoting around the user's ear. This rotation increases the distance from the MRP to the device's microphones, but does not increase the distance from the user's ear to the device's speaker significantly.

FIG. 4 illustrates exemplary ILD equalization (EQ) curves for five positions of the MRP relative to the device's microphones. The ILD EQ chart plots normalized ILD (y-axis) vs. frequency sub-bands (x-axis) as used in the cochlear domain. In FIG. 4, the legend at the bottom of the chart labels five positions (410, 420, 430, 440, and 450) as: nominal position, rotated 30 degrees positive, rotated 30 degrees negative, pivoted 30 degrees positive, and pivoted 30 degrees negative respectively. Curve 415 is associated with position 410, curve 425 with position 420, curve 435 with position 430, curve 445 with position 440, and curve 455 with position 450. When the communication device is moved from its nominal position, different EQ curves may thus be used for optimal correction of ILD distortion. Hence, for a given normalized ILD, sub-band, and positional information, a corresponding equalization function may be applied to the normalized ILD signal to correct distortion. The equalization function may be applied to the normalized ILD signal by either the source inference engine 306 or mask generator 308. In one embodiment, positional information from non-acoustic sensors that include a relative spatial position, such as an angle of rotation or pivot, can be used to select the most appropriate curve from a plurality of ILD equalization arrays.

As discussed above with respect to source inference engine 306, non-acoustic sensor information may be used to configure a gain of a microphone signal as processed, for example, by feature extraction module 304. Specifically, in multi-microphones systems that use ILD as a source discrimination cue, the level of the main speech decreases as the distance from the primary microphone to the MRP increases. ILD cue corruption typically leads to undesirable speech loss. Increasing the gain of the primary microphone modifies the ILD in favor of the primary microphone.

Some of the scenarios in which the present technology may advantageously be leveraged are: detecting when a communication device is passed from a first user to a second user, detecting proximity variations due to a user's lip, jaw, and cheek motion and correlating that motion to active speech, leveraging a GPS sensor, and distinguishing speech vs. noise based on correlating accelerometer cues to distant sound sources while the communication device is in close proximity to the MRP.

Figure 5A:
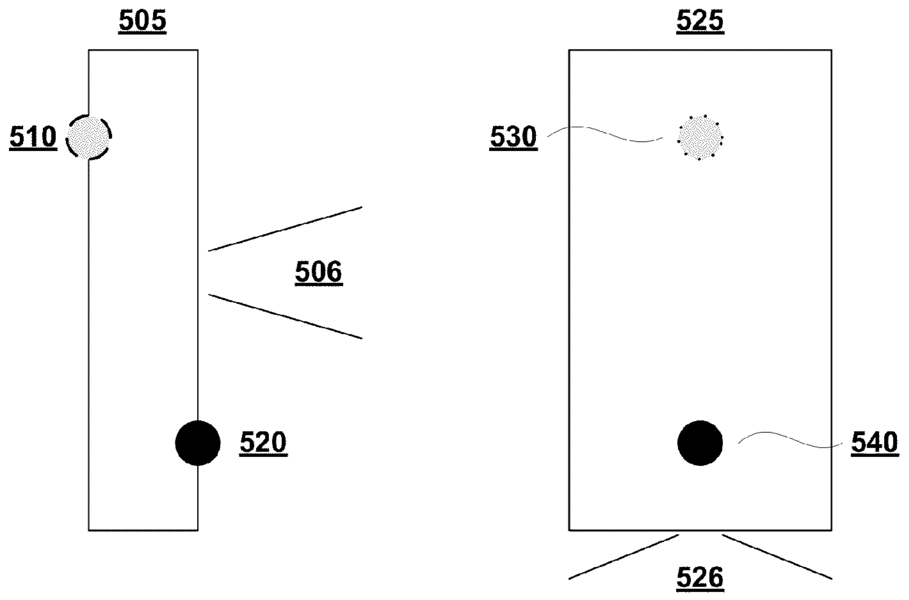
FIG. 5A illustrates orientation-dependent receptivity of a communication device in a vertical orientation.

FIG. 5A illustrates orientation-dependent receptivity of a communication device in a vertical orientation. Devices 505 and 525 are shown using different viewing angles of a similar device having the shape of a rectangular prism (a.k.a a rectangle). Microphones 520 and 540 are the primary microphones located on the front of a device. Microphones 510 and 530 are the secondary microphones located on the back of a device. Device 505 is shown vertically from the side, whereas device 525 is shown vertically from the front, such that microphone 530 is obscured from view by the body of device 525. Cone 506 indicates the area of highest receptivity for the position of device 505, and extends in the third dimension (perpendicular to the page) by rotating cone 506 around the center of device 505, creating a torus extending horizontally around device 505. Similarly, for device 525, its area of highest receptivity is indicated by cone 526, which extends in the third dimension towards the reader, rotated horizontally, perpendicular to the page, around device 525, creating a torus. When device 505 or 525 is thus positioned vertically, moving the MRP from its nominal position from left to right or vice-versa effects the processing of the received acoustic signal differently than moving the MRP up or down from its nominal position. Sensor information from non-acoustic sensors may be used to counter such effects, or counter the change of a device from horizontal to vertical orientation or vice-versa.

Figure 5B:
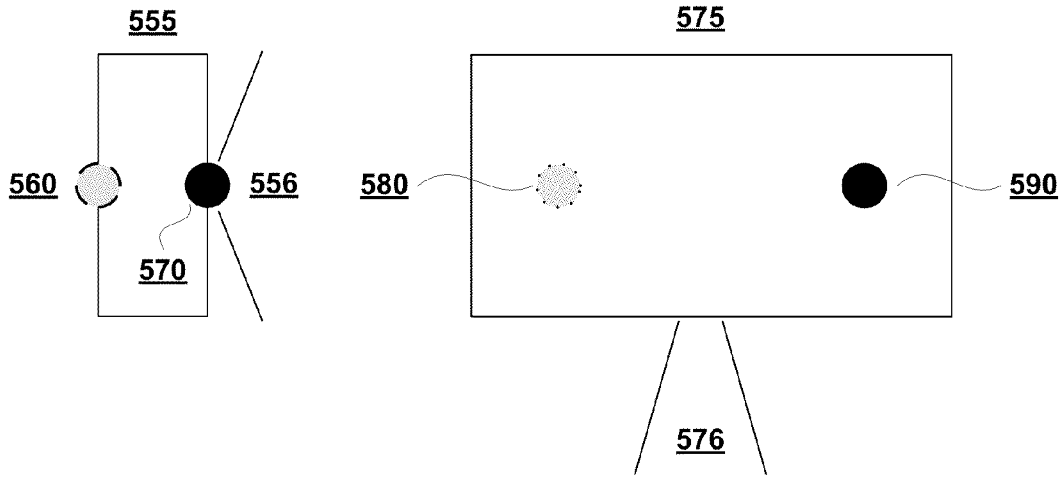
FIG. 5B illustrates orientation-dependent receptivity of a communication device in a horizontal orientation.

FIG. 5B illustrates orientation-dependent receptivity of a communication device in a horizontal orientation. Devices 555 and 575 are positioned sideways, for example as if devices 505 and 525 in FIG. 5A were rotated by 90 degrees towards the reader (in the third dimension, off the page) and anti-clockwise respectively. Device 555 and 575 are shown using different viewing angles of a similar device having the shape of a rectangular prism. Microphones 570 and 590 are the primary microphones located on the front of a device. Microphones 560 and 580 are the secondary microphones located on the back of a device. Device 555 is shown horizontally from the top, whereas device 575 is shown horizontally from the front, such that microphone 580 is obscured from view by the body of device 575. Cone 556 indicates the area of highest receptivity for the position of device 555, and extends in the third dimension (perpendicular to the page) as if the torus around device 505 were rotated by 90 degrees towards the reader (in the third dimension, off the page). Similarly, for device 575, its area of highest receptivity is indicated by cone 576, as if the torus around device 525 were rotated by 90 degrees anti-clockwise. When device 555 or 575 is thus positioned horizontally, moving the MRP from its nominal position from left to right or vice-versa effects the processing of the received acoustic signal differently than moving the MRP up or down from its nominal position. Sensor information from non-acoustic sensors may be used to counter such effects, or counter the change of a device from horizontal to vertical orientation or vice-versa.

Figure 6:
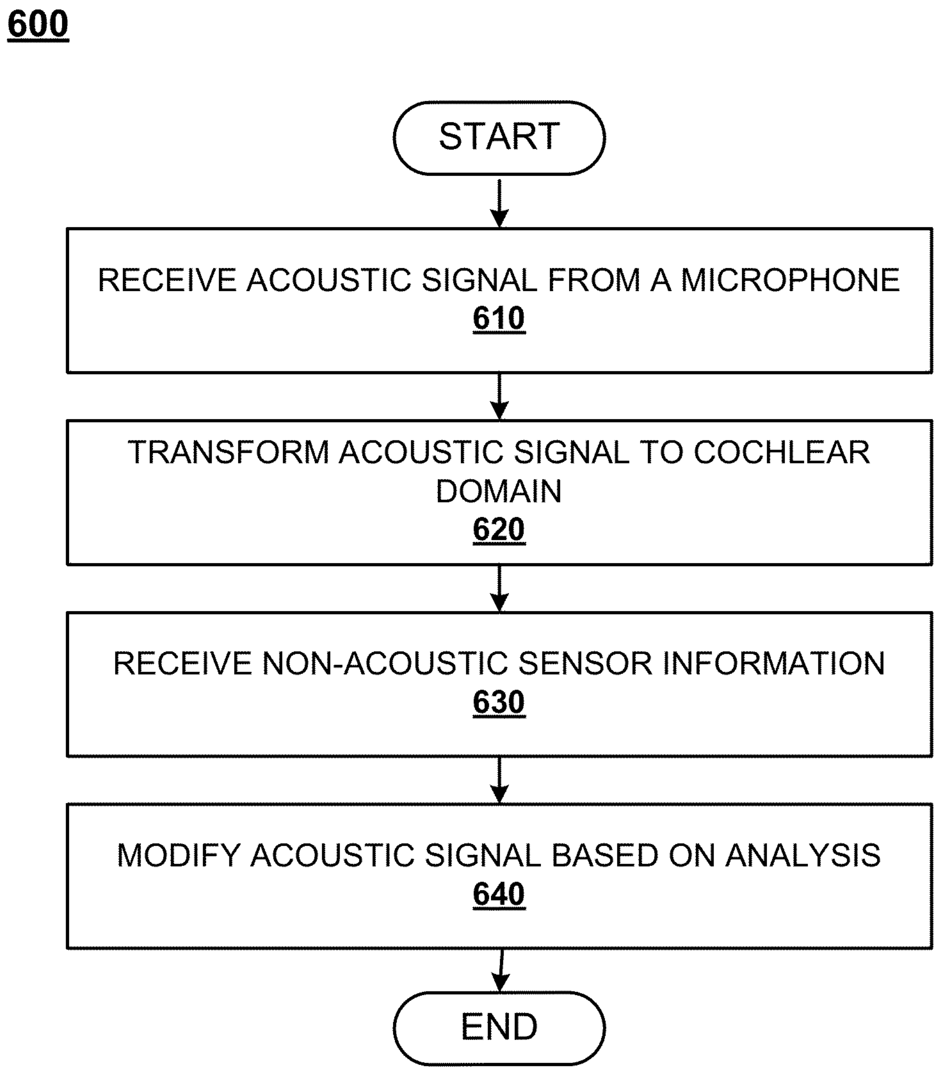
FIG. 6 illustrates a flow chart of an exemplary method for audio processing.

FIG. 6 illustrates a flow chart of an exemplary method 600 for audio processing. An acoustic signal is received from a microphone at step 610, which may be performed by microphone 106 (FIG. 1) providing a signal to audio processing system 210 (FIG. 3). The received acoustic signal is optionally transformed to the cochlear domain at step 620. The transformation may be performed by frequency analysis module 302 in audio processing system 210 (FIG. 3). Non-acoustic sensor information is received at step 630, where the information may be provided by non-acoustic sensor 120 (FIG. 2), and received as sensor data 325 in FIG. 3 by analysis path sub-system 320. The received, and optionally transformed, acoustic signal is modified based on an analysis of the received, and optionally transformed, acoustic signal and the received non-acoustic sensor information at step 640, wherein the analysis and modification may be performed in conjunction by analysis path sub-system 320 and signal path sub-system 330 (FIG. 3) in general, or any of the (sub-) modules included therein respectively. Adjustments of some system parameters such as gain may be performed outside of analysis path sub-system 320 and signal path sub-system 330, but still within communication device 104.

The present technology is described above with reference to exemplary embodiments. It will be apparent to those skilled in the art that various modifications may be made and other embodiments can be used without departing from the broader scope of the present technology. For example, embodiments of the present invention may be applied to any system (e.g., non speech enhancement system) utilizing acoustic echo cancellation (AEC). Therefore, these and other variations upon the exemplary embodiments are intended to be covered by the present invention.

The invention claimed is:

1. A method for audio processing, comprising:

receiving a first acoustic signal from a first microphone;

receiving a second acoustic signal from a second microphone;

receiving information from a first non-acoustic sensor; and executing a module by a processor, the module executable to determine a set of parameters to use to modify the first acoustic signal based at least in part on the first acoustic signal, the second acoustic signal, and the first non-acoustic sensor information;

wherein the modifying is performed using at least one of noise suppression, echo cancellation, audio source separation, and equalization.

2. The method of claim 1, further comprising generating a plurality of frequency sub-bands, and wherein modifying is performed per frequency sub-band.

3. The method of claim 1, wherein the first non-acoustic sensor is selected from the group consisting of a motion sensor, a light sensor, a proximity sensor, a gyroscope, a level sensor, a compass, a GPS unit, and an accelerometer.

4. The method of claim 1, wherein the first non-acoustic sensor measures a spatial position of a microphone relative to a spatial position of an audio source.

5. The method of claim 1, further comprising receiving information from a second non-acoustic sensor, wherein the determining of the set of parameters is further based on analysis of the information from the second non-acoustic sensor;

the first non-acoustic sensor and the second non-acoustic sensor each being selected from the group consisting of a motion sensor, a light sensor, a proximity sensor, a gyroscope, a level sensor, a compass, a GPS unit, and an accelerometer.

6. The method of claim 1, wherein modifying is further based on noise suppression via null processing.

7. The method of claim 1, wherein the parameters include a respective gain for one or more of the first and second acoustic signals.

8. The method of claim 1, wherein the parameters include an inter-level difference equalization.

9. The method of claim 6, wherein the parameters include directionality coefficients.

10. The method of claim 1, wherein the information of the first non-acoustic sensor includes proximity variations that indicate active speech.

11. A system for audio processing, comprising:

a first microphone that transduces a first acoustic signal, wherein the first acoustic signal includes a desired component and an undesired component;

a second microphone that transduces a second acoustic signal;

a first non-acoustic sensor that provides non-acoustic information; and one or more executable modules for determining a set of parameters to use to modify the first acoustic signal based on the first acoustic signal, the second acoustic signal, and non-acoustic sensor information;

wherein the modifying is performed using at least one of noise suppression, echo cancellation, audio source separation, and equalization.

12. The system of claim 11, wherein an executable module of the one or more executable modules further includes reducing the undesired component of the first acoustic signal.

13. The system of claim 11, wherein an executable module of the one or more executable modules further includes analyzing the first acoustic signal.

14. The system of claim 11, wherein the first non-acoustic sensor is selected from the group consisting of a motion sensor, a light sensor, a proximity sensor, a gyroscope, a level sensor, a compass, a GPS unit, and an accelerometer.

15. The system of claim 11, wherein the first non-acoustic sensor measures a spatial position of the first microphone relative to a spatial position of a source of the acoustic signal.

16. The system of claim 11, wherein an executable module of the one or more executable modules implements noise reduction via signal component subtraction.

17. A non-transitory computer readable storage medium having embodied thereon a program, the program being executable by a processor to perform a method for audio processing, the method comprising:

receiving a first acoustic signal from a first microphone;

receiving a second acoustic signal from a second microphone;

receiving information from a first non-acoustic sensor; and determining a set of parameters to use for modifying the first acoustic signal based at least in part on the first acoustic signal, the second acoustic signal, and the first non-acoustic sensor information;

wherein the modifying is performed using at least one of noise suppression, echo cancellation, audio source separation, and equalization.

18. The non-transitory computer readable storage medium of claim 17, wherein modifying is further based on noise reduction via signal component subtraction.

* * * * *